United States Patent [19]

Forrest et al.

[11] 4,141,687
[45] Feb. 27, 1979

[54] AUTOMATIC APPARATUS AND METHOD FOR THE ASSAY OF FLUID SAMPLES

[75] Inventors: Gordon C. Forrest, Chelmsford; Ronald F. Jay, New Malden; John A. Clements, Wallington, all of England

[73] Assignee: Technicon Instruments Corporation, Tarrytown, N.Y.

[21] Appl. No.: 776,443

[22] Filed: Mar. 10, 1977

[30] Foreign Application Priority Data

Mar. 12, 1976 [GB] United Kingdom ............... 10089/76

[51] Int. Cl.² ..................... G01N 33/16; G01N 27/74
[52] U.S. Cl. ............................. 23/230 R; 23/230 B; 195/103.5 A; 252/408; 424/1; 210/222; 210/42 S; 422/67; 422/81; 422/82
[58] Field of Search ............. 23/230 R, 253 R, 230 B; 424/1; 195/103.5 A; 252/408; 210/222, 223, 42 S

[56] References Cited

U.S. PATENT DOCUMENTS 3,933,997 1/1976 Hersh et al. ................. 23/230 B

OTHER PUBLICATIONS

Robinson, P. J. et al., (1973) Biotechnol. Bioeng. 15, pp. 603–606.
Hersh et al., (1975), Clin. Chem. Acta. 63, pp. 69–72.
Nye, L. et al., (1976) Clin. Chem. Acta. 69, pp. 387–396.
Pollard et al., Automation in Analytical Chemistry, (1972), vol. 1, pp. 61–67, Mediad, N. Y.
Bagshawe et al., Automation in Analytical Chem., (1967), vol. 2, pp. 53–56, Mediad, N. Y.
Johnston et al., Automation in Analytical Chem., (1972), vol. 1, pp. 69–72, Mediad, N. Y.
Luner, (1975), Anal. Biochem, 65, pp. 355–361.

Primary Examiner—R.E. Serwin
Attorney, Agent, or Firm—S. P. Tedesco; R. S. Salzman

[57] ABSTRACT

Method and apparatus suitable for automatic assay of fluid samples, particularly immunoassays, in which a reaction product of the assay is bound to a magnetically attractable particle and separated from the reaction mixture by use of a magnetic trap. The method and apparatus are of especial use in radioimmunoassays carried out in an automated continuous-flow manner.

67 Claims, 6 Drawing Figures

AUTOMATIC APPARATUS AND METHOD FOR THE ASSAY OF FLUID SAMPLES

This invention is concerned with a method and apparatus for analysing a fluid sample, particularly but not exclusively for use in immunoassays.

It is known to assay biological fluids such as blood serum or urine to detect and quantify the presence therein of antibodies (and similar binding proteins), antigens (and similar substances such as haptens) and antibody-antigen immune complexes. Such procedures are broadly called immunoassays. One common technique in immunoassays is to make use of the binding reaction which takes place between a limited amount of an antibody and two antigens, both antigens being capable of binding with the antibody but being distinguishable, e.g. in that one antigen carries an identifying label. The proportion of labelled antigen which binds with the antibody gives an indication of the amount of unlabelled antigen present. Thus, if for example a biological fluid sample containing a specific antigen is mixed with antibody and an amount of labelled antigen, the amount of (unlabelled) antigen in the sample can be determined.

Various labels have been suggested, but the most successful has been a radioactive label and immunoassays using radioactive labels are called "radioimmunoassays" (RIA).

In immunoassay procedures, it is often necessary to separate the reaction product (e.g. the antibody-antigen complex) from the reaction mixture in order for example to determine the amount of labelled antigen in the product (by direct analysis either of the product or of the remaining reaction mixture). It has been suggested in the prior art that in RIA procedures (in which a separation step is essential), the antibody be immobilised on a carrier to facilitate subsequent separation of the reaction product. Thus, in "Continuous Flow Automated Radioimmunoassay Using Antibodies Attached to Red Blood Cells", by S. J. Luner, *Analytical Biochemistry*, Vol. 65 (1975), pages 355-364, it is said that red blood cells may be used for the immobilisation of antibodies in automated RIA techniques using a continuous-flow system.

In "Magnetic Solid-Phase Radioimmunoassay" by L. S. Hersh and S. Yaverbaum, *Clinica Chemica Acta*, Vol. 63 (1975), pages 69-72, antibody is immobilised on magnetic particles and the reaction product separated from the reaction mixture by application of a magnetic field. This RIA procedure is carried out in a test tube reactor, and the supernatant reaction mixture is assayed.

We have now devised a continuous-flow method of effecting immunoassays, and apparatus useful for this purpose, in which magnetic particles are used and by which a series of liquid samples can be successively and automatically assayed by, for example, RIA.

In one aspect, the invention provides a method of analysing a biological fluid for a constituent of interest, which comprises the steps of:

(a) forming a mixture of a sample of the fluid and a solid phase comprising a reagent bound to a magnetically attractable particulate material;

(b) flowing the mixture along a conduit;

(c) magnetically trapping the solid phase in the conduit to hold the particulate material against flow and thereby to separate the solid phase from the mixture; and (d) determining the constituent of interest in the sample by analysis on the separated solid phase and/or separated mixture.

In another aspect, the invention provides analysis apparatus which comprises means for flowing along a conduit a reaction mixture comprising a liquid phase including a fluid sample containing a constituent of interest, and a solid phase comprising a reagent bound to magnetically attractable particulate material, reaction taking place in the said mixture to form a reaction product on said solid phase; means for magnetically trapping the particulate material in said conduit to hold it against flow and so to separate the solid phase from the flowing liquid phase; and, downstream of said trapping means, means for determining the constituent of interest in the sample by analysis of the separated solid phase or liquid phase.

In the method of the invention, and in the use of the apparatus, a reaction mixture is flowed along a conduit. The mixture comprises the sample under test which includes the constituent of interest, i.e. the substance which is to be assayed. In the case, for example, of biological fluids such as blood serum, the constituent of interest may, for example, be an antigen, e.g. a peptide hormone, a steroid hormone, a drug or a virus (the term "antigen" is intended to include haptens and other similar substances), an antibody (which term includes other binding substances), or an antibody: antigen complex, or a single protein. The invention is not limited, however, to the assay of biological fluids.

The reaction mixture also includes, as a solid phase, magnetically attractable particulate material which has a reagent bound thereto. This particulate material may itself be a composite material made up of, for example, a matrix containing magnetically attractable material, with the reagent bound to the particle. Such a material is itself novel and constitutes a further aspect of the present invention. The magnetically attractable material may be, for example, iron or magnetic iron oxides, nickel, cobalt or chromium oxide. Suitably, one or more particles of such a material are embedded in the matrix. The matrix itself may be of a wide variety of materials including many synthetic and natural polymeric materials (e.g. cellulose, cellulose derivatives, agarose, organic polymers). The reagent may be bound directly to the matrix or to another material within the matrix.

The reagent itself is a substance which takes part in a reaction in the reaction mixture. It may react directly with the constituent of interest in the sample, or it may react not directly with the sample but with a second reagent in the mixture. Thus, for example, the reagent on the particulate matter may be an antibody which will react directly with an antigen in the sample under test, or the sample itself may contain an antibody and the reagent react with an antigen added as the second reagent. In the latter case, the second reagent antigen may also react with the antibody in the sample.

The reagent is bound to the particulate material in such a manner that the reagent is available to react with another substance in the reaction mixture. Usually, there will be reagent bound to the peripheral surface of the particulate material, but this is not essential provided that the reagent is accessible for reaction. The reagent may thus be wholly within the matrix but in such case, the matrix will be porous to the liquid of the reaction mixture.

The nature of the reagent can vary very widely, depending on the particular analysis to be performed. It may, for example, be an immunoglobulin, an antigen (e.g. a virus) or another biological substance. After reaction, it remains bound (as reaction product) to the particulate material and is thus separated with the particulate material from the reaction mixture.

The separation of the particulate material solid phase from the liquid phase of the reaction mixture is effected in the conduit using a magnetic trap. The reaction mixture flows along the conduit into the region of a localised magnetic field (the magnetic trap), whereupon the solid phase is held by the field whilst the liquid phase flows on.

Preferably, the magnetic field is disposed in the conduit substantially transversely of the flowing reaction mixture, but this is not essential. As will be clear, the strength of the field must be sufficient to hold the solid phase against the liquid flow.

After the liquid has passed through the trap, the solid phase in the conduit can be washed by passing a wash liquid through that portion of the conduit. The solid phase remains held in the trap but the particles are exposed to, and washed by, the wash liquid flowing past. It is a highly advantageous preferred feature of the present invention to be able to wash the solid phase "on line" and thus the apparatus of the invention preferably comprises means for passing wash liquid along the conduit.

The wash liquid may be water or any inert fluid or solution, its purpose being to remove from the solid phase remaining traces of the reaction mixture liquid phase. This is particularly important in immunoassays, such as RIA, where the solid phase is to be assayed for the presence of a label, since in such cases even trace residues of the reaction mixture liquid phase could lead to incorrect assay results.

The magnetic field is preferably provided by at least one magnet means actuable to provide magnetic field in a portion of the conduit. The (or each) magnet means may be a permanent magnet which is moveable to vary the field from a minimum (when the trap is "deactuated") to a maximum when the trap is "actuated"). We prefer, however, to use one or more electromagnets. Upon deenergisation of the electromagnet, it is preferable to degauss by providing an alternating current, thus ridding the electromagnet of residual magnetic field. Solid phase in the trap will also be demagnetised by this procedure, thus reducing any tendency to clogging due to magnetic attraction.

The magnetic trap may consist of a single magnet means, or two or more such means. For many purposes, it is preferred to provide two (or more) magnetic traps, spaced apart along the conduit. This enables an improved washing procedure, for example, to be effected. Thus, with two traps, the magnet means of each trap are actuable independently of each other, and the solid phase is separated from the liquid phase of the reaction mixture in the first (upstream) trap. It is washed whilst it is held in that trap, and then the trap is deactuated to release the solid phase into suspension in flowing wash liquid. The particulate matter is carried to the second trap (which is energised) and held against the wash liquid flow. This double wash procedure is particularly effective.

The liquid phase of the reaction mixture passes through the magnetic trap(s) and flows further along the conduit. Similarly, after washing, the solid phase is released from the trap and passes along the washed conduit. Preferably, valving means are provided in the conduit for directing the separated solid phase or liquid phase to the analysis means as required. If the solid phase is to be analysed, the liquid phase of the reaction mixture can be collected in a receiver or passed to waste. If the liquid phase is to be measured (possibly together with wash liquid), the solid phase may be passed to a receiver, and possibly (after treatment) reused. It will usually be preferable to assay the solid phase because it can be automatically washed (as described above), whereas the liquid phase is likely to be bulky (with the wash liquid) and not so easily handled or analysed.

The constituent of interest in the sample is determined by analysis of the separated solid or liquid reaction mixture phases. It will be appreciated that this determination may involve several analytical and/or calculation steps. Thus, in the case of RIA, analysis of the solid phase by counting the radioactivity, will reveal the amount of radioactive label in the solid phase. From this, and standard curves, it will be possible to determine the amount of constituent of interest in the sample.

It is possible according to the invention to effect further reactions on the separated solid or liquid phase, and to introduce further magnetically attractable particles for a subsequent separation step. This may be desirable, for example, when the reaction mixture contains an enzyme or co-enzyme. In such cases further magnetic traps may be provided in the circuit downstream of the trap(s) for effecting the first separation.

In the method of the invention, and in use of the apparatus, the whole or any part of the reaction mixture may be preformed before it is flowed along the conduit. It is usually preferred, however, to add one or more reagents to the flowing sample (or partly formed mixture) in the conduit. Thus, the apparatus preferably includes means for introducing the said particulate material and/or the second reagent into admixture with the flowing sample (or reaction mixture) in the conduit. Intermixing of the sample and the reagents will take place in the conduit as the mixture flows (as is described more fully hereinafter).

Whilst we have specifically referred above to the reagent bound to the particulate material, and to the second reagent, it will be understood that there may also be other reagents present in the reaction mixture. These other reagents may be added in admixture with the particulate material or second reagent, or they may be pre-mixed with the sample, or they may be added individually to the flowing sample (or reaction mixture) in the conduit. The nature of these reagents (if any are used) will be determined by the nature of the assay being performed. The reaction mixture may also contain other substances such as buffers.

In immunoassays involving binding between, for example, an antibody and an antigen, the second reagent will usually carry an identifying label such as a radioactive atom, a fluorescent group, an enzyme or co-enzyme or a chemiluminescent material. Thus, for example, when the biological fluid sample is to be assayed for an antigen, the reagent on the particulate material will be an antibody for binding with the antigen, and the second reagent will be an antigen capable of binding with the antibody and which also carries a label. In the alternative, the fluid sample may be assayed for antibody by providing an antigen on the particulate material and using a labelled antibody as the second reagent. As will be understood by those skilled in the art, analysis of the separated solid phase or liquid phase for the amount of label present will allow determination of the amount of constituent of interest in the fluid sample.

The particular analysis to be carried out on the separated solid or liquid phases will depend on the assay being effected and (where a labelled reagent is used) on the nature of the label. Thus, the apparatus of the invention may include, for example, means for measuring the radioactivity, the colour or fluorescence of the separated phase or its enzymic activity.

It will be understood that it is not essential in the method of the invention to use a second or any reagent other than that bound to the particulate matter. Thus, the method (and apparatus) can be used, for example, to separate a particular constituent from a fluid sample (by selectively binding it to the reagent on the particulate material) and then subsequently assaying the separated solid phase. In most immunoassay procedures, however, a second reagent is used (and there may often be other reagents too).

The method and apparatus of the invention may be used in the known continuous-flow type of procedure in which individual segments of reaction mixture are passed along the conduit, separated by an inert fluid segment (e.g. air) and, if desired, a wash liquid segment. This is described in U.S. Pat. No. 2,797,149 to which reference should be made for further details. Thus, the apparatus of the invention preferably includes means for passing successive reaction mixtures along said conduit separated from each other by at least an inert fluid segment of sufficient volume to occlude said conduit and maintain said successive mixtures discrete. The apparatus may also include means for introducing inert fluid segments into said conduit to subdivide liquid samples or reaction mixtures therein. Further, the apparatus preferably includes means for providing a wash liquid segment between successive reaction mixtures flowing in said conduit, each said mixture being separated from adjacent wash liquid segments by at least an inert fluid segment.

When the reaction mixture (or sample) is segmented, and the particulate material and/or the second reagent is to be added to the flowing segments in the conduit, then means are provided for introducing the particulate material (and/or the second reagent) on an intermittent basis so that they merge with successive sample segments in the conduit. Preferably, the intermittent introducing means includes means for returning particulate material not admitted to the conduit, to a reservoir therefor. Preferably, also, the apparatus includes means for introducing buffer solution into said conduit alternately with said particulate material, so as (in use) to maintain the flow along said conduit substantially constant.

It will be appreciated that it is important that any labelled reagent (or other reagent of critical importance in the final determination procedure) be added only to the sample or reaction mixture, and not to any wash liquid or other segments in the conduit, since otherwise an incorrect assay may result.

It is convenient, particularly when segmented flow is used, to provide in the apparatus upstream of the magnetic trap(s) a sensing means to detect the passage of a reaction mixture along the conduit and to provide means for actuating the magnetic trap to trap the particles in that reaction mixture, in response to the sensing means. Depending on how far upstream of the trap the sensing means is located, a time delay may be needed before actuation.

The particulate matter will preferably have a specific gravity close to that of the liquid phase of the reaction mixture, so that it does not tend to settle out (nor to float to the top) but rather remains in good admixture in suspension. Generally, the particulate matter will have a specific gravity substantially in the range of about 1.4 to 3.2, although values outside this range can be used.

It will be understood that, in the method of the invention (and in use of the apparatus) sufficient time must be allowed after forming the reaction mixture for the desired reaction(s) to take place, before the solid phase is separated from the liquid phase. To provide this period (commonly called "incubation"), the conduit may include, for example, an incubation coil.

In one preferred method of the invention, the reaction mixture comprises, as second reagent, a predetermined amount of a substance which reacts with the constituent of interest to form therewith a complex, and wherein the reagent on the particulate material binds either with the complex or with excess unreacted second reagent, and wherein in step (d) the separated mixture is analysed to determine the constituent of interest in the sample. In this method, the analysis is carried out either for the complex or for the excess unreacted second reagent, as appropriate.

In another method of the invention, antibody in a sample is assayed using, as the reagent on the particulate material, an antibody and, as the second reagent, an antigen (labelled) which will bind with both antibodies (both antibodies may be the same).

It will be understood that, in the method of the invention (and in the use of the apparatus), control over the quantities of reagents used is effected as appropriate. Thus, in RIA, using a radioactively labelled second reagent, for example, the amount of second reagent present (or the amount of label) in the reaction mixture will be controlled and known.

The method and apparatus of the invention can advantageously be automated. As such they can provide a highly efficient compact unit, especially useful for immunoassays, particularly RIA.

In order that the invention may be more fully understood, one embodiment thereof will now be described, by way of example only, with reference to the accompanying drawings, in which.

Figure 1:
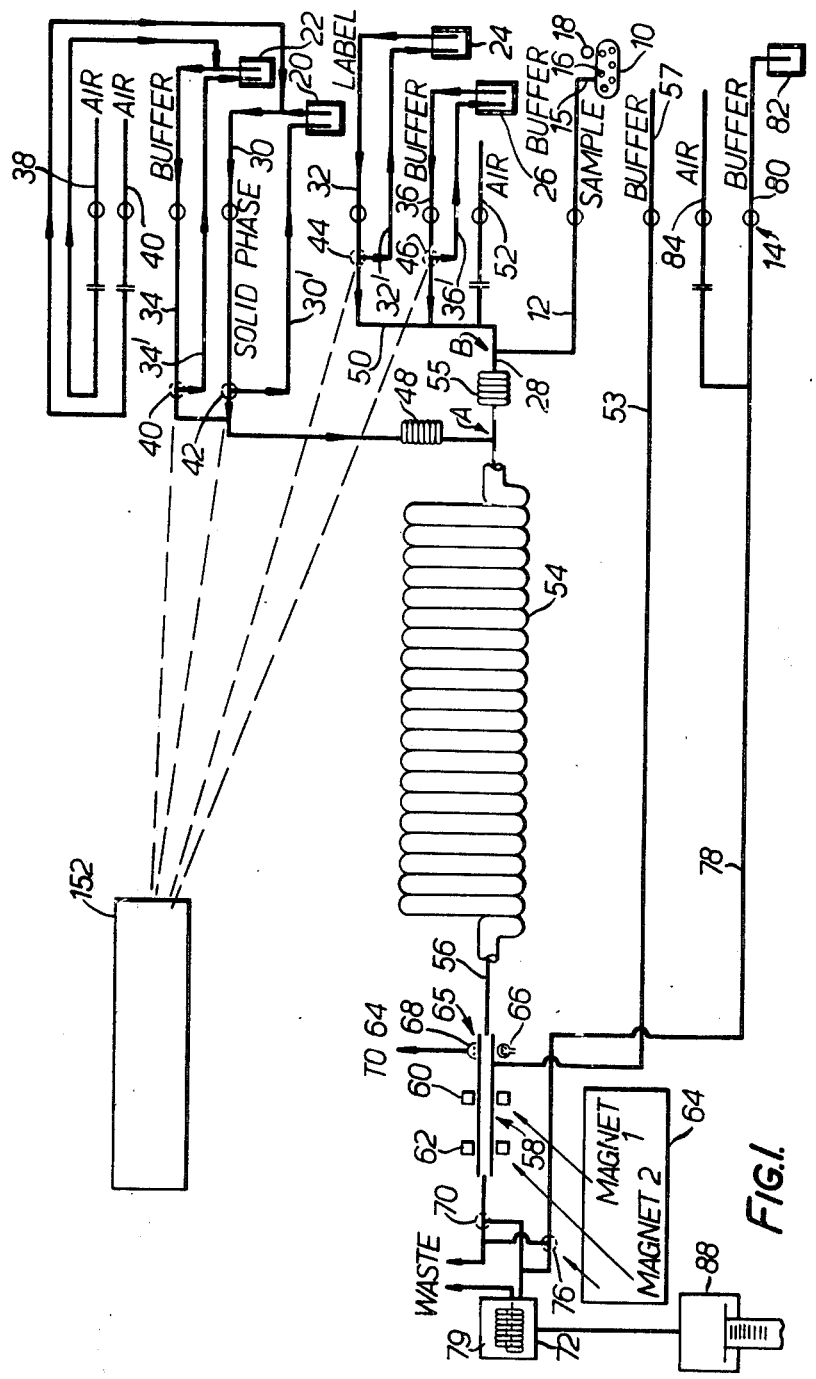
FIG. 1 is a flow diagram of one form of apparatus according to the present invention.

Referring now to the drawings, there is shown a sampler arrangement 10 for supplying a series of liquid samples along a compressible pump tube 12. Sampler arrangement 10 may be of the type shown and described in U.S. Pat. No. 3,038,340. Pump tube 12 is incorporated in a peristaltic-type pump 14, of the type described in U.S. Pat. No. 2,935,028 (which also controls tubes 38, 40, 34, 34', 30, 30', 32, 36, 52, 57, 84 and 80 as hereinafter described). Probe 15 is controlled to be immersed alternately in successive sample receptacles 16, and a wash receptacle 18. As the probe 14 aspirates air between immersion into successive sample receptacles 16 and wash reservoir 18, the sample stream directed along pump tube 12 comprises successive samples, each separated from adjacent samples by air-wash liquid-air segments. Accordingly, sample integrity is maintained during flow along the entire system, as hereinafter described. In addition to sampler 10, a source 20 of antibodies immobilized on the surface of magnetically attractable particles in suspension, an associated source 22 of the buffer solution, a source 24 of a labelled antigen in solution, and an associated source 26 of buffer, are provided. The system is operated such that the solid phase from source 20, appropriately buffered, and the labelled antigen from source 24, appropriately buffered, are introduced in controlled discrete volumes and proper phases, to be mixed only with successive samples pumped along pump tube 12 and conduit 28. To this end, pump 14 comprises a plurality of pump tubes, 30, 32, 34 and 36 having respective inlets in fluid communication with source 20 of the solid phase, source 24 of the labelled antigen and the associated buffer sources 22 and 26. Also, pump tubes 38 and 40 are provided for periodically injecting air bubbles to segment the fluid streams passed along pump tubes 30 and 34, to provide discrete segments of uniform concentration of the solid phase and maintain a constant flow rate through the system when valves 40 and 42 are operated. Each of the pump tubes 30, 32, 34 and 36 has an associated return conduit 30', 32',34' and 36', respectively, whereby fluid is recirculated back to the respective sources 20, 24, 22 and 26. The outlets of pump tubes 30, 32, 34 and 36 are connected to the inlets of three port-two-position valves, 42, 44, 40 and 46, respectively. One outlet of each such valve is connected to the associated return conduit. The remaining outlets of valves 40 and 42, associated with the solid phase, are multipled and connected along a mixing coil 48 to conduit 28 at junction A. Also, the remaining outlets of valves 44 and 46 are multipled and connected along conduit 50 to conduit 28 at junction B. Additionally, the outlet of pump tube 52, having an inlet exposed to air, is connected to segment the liquid stream along conduit 50 prior to introduction into conduit 28. As peristaltic pump 14 operates continuously, air segments are continuously injected via air pump tubes 38, 40 and 52 so as to achieve both intrasample segmentation and intra-wash liquid segmentation, as hereinafter described, whereby effective internal mixing of the individual segments of the flowing stream along conduit 28 is obtained.

Valves 40, 42, 44 and 46 are controlled by a programmer 152, which is timed with respect to sampler 10, such that the buffered labelled-antigen stream along conduit 50 and the buffered solid phase along mixing coil 48 are introduced in discrete volumes and in proper phase at junctions B and A, respectively, to be intermixed only with each liquid sample along conduit 28. During passage of the wash liquid segment (intermediate successive samples) along junction A and also along junction B, valves 42 and 44 are operated to position I, to interconnect pump tubes 30 and 32 with conduits 30' and 32', respectively, and recirculate the liquids being passed therealong to their sources. Simultaneously, valves 40 and 46 are operated to position II, to direct the buffer solution from sources 22 and 26, respectively, to junctions A and B, to maintain constant flow rates along conduit 28. At this time, air is being pumped constantly along pump tube 52, whereby air bubbles are periodically injected into conduit 50 to segment the fluid stream therealong and direct it to junction B, to ensure proper mixing along coil 55. During passage of a sample along junctions A and B, programmer 152 operates valves 42 and 44 momentarily to position II, to introduce controlled discrete volumes of the buffered solid phase along mixing coil 48 and of the labelled antigen suspension along conduit 50 into such sample. A mixing coil 55 is provided along conduit 28 and intermediate junctions A and B, to ensure that the labelled antigens are thoroughly mixed and uniformly distributed throughout each liquid sample segment, prior to introduction of the solid phase at junction A.

Figure 2:
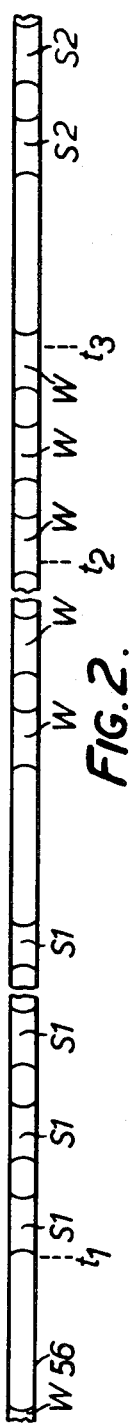
FIG. 2 illustrates the composition of the fluid stream passed along the system of FIG. 1.
Figure 3A:
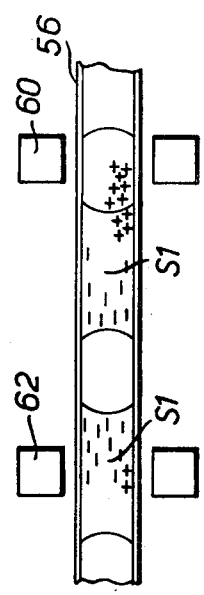
FIGS. 3A–3C illustrate the operation of the on-line magnetic traps to effect separation and working of the solid phase.
Figure 3C:
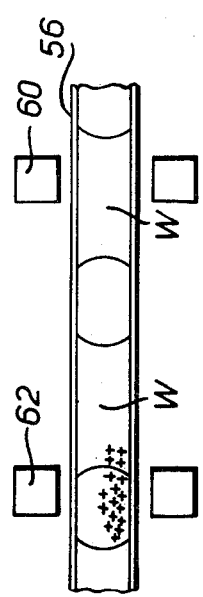
Figure 2A:
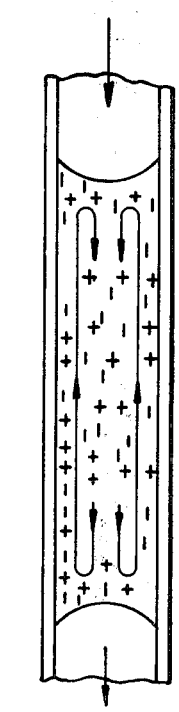
FIG. 2A illustrates the two-phase laminar flow pattern within the fluid samples of FIG. 2.
Figure 3B:
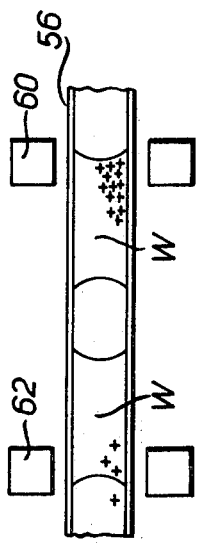

The successive sample segments, co-mixed with the solid phase and labelled antigen to form reaction mixture, are directed along conduit 28 to an incubation coil 54. The composition of the stream directed to the incubation 54 is illustrated in FIG. 2. Each of the segments, or aliquots, of sampls $S_1$, $S_2$, etc. include controlled volumes of the solid phase and labelled antigen; the wash liquid segments (W) are between successive samples and the successive samples are themselves segmented by air bubbles introduced along pump tube 52. In FIG. 2A, the labelled antigen and the solid phase, i.e. antibodies immobilized on magnetically attractable particles, are distributed throughout a sample aliquot and are indicated by "—" and "+", respectively. The presence of air segment immediately preceding and following a liquid segment induces a two-phase laminar flow pattern, whereby the liquid in such segment is caused to recirculate, as indicated by the arrows in FIG. 2A. Such flow pattern results, primarily, from the drag imposed on the moving liquid immediately at the inner surface of conduit 28, and serves to accelerate the mixing of the various components of the reaction mixture.

As described, the solid phase comprises magnetically attractable particles of controlled specific gravity. Preferably, these particles comprise a matrix having one or more small ferromagnetic particles embedded therein. For example, the ferromagnetic particles may be coated with an organic material, e.g. a polymeric material, or they may be silanized, to bind with either an antibody or antigen. For example, suitable coating techniques have been described in the above-identified Hersh and Yaverbaum article and, also, in "The Properties of Magnetic Supports in Relation to Immobilized Enzyme Reactions", P. J. Robinson et al, *Biotechnology and Bioengineering*, Vol. XV. (1973) pp603–606. The ratio of the respective volumes of the matrix and the magnetic particles is chosen so that the resulting specific gravity approaches that of the liquid phase. As such, these magnetically attractable particles are carried along by the two-phase laminar flow pattern induced within each sample aliquot and do not tend to settle out, either by gravitation or flotation. It should be appreciated that the specific gravity of the magnetic particles need not be equal to the specific gravity of the liquid phase, but should be such as to avoid settling or flotation of the solid phase during passage through the system. The reduced density of such particles provides for excellent wash characteristics, whereby there is substantially no contamination between successive samples. For example, if the particles were to have a specific gravity much higher than that of the liquid phase, they would tend to settle out and collect in the cusp defined at the interface between the sample aliquot and the up-stream air segment along the inner wall surface of conduit 28. Such settling would substantially increase the possibility that such particles could pass under the up-stream air segment, and following liquid and air segments in the flowing stream to contaminate a following sample. If the specific gravity of the particles is reduced much below that of the sample, the particles separate out by flotation and may possibly pass over the following liquid and air segments to effect contamination. By controlling the specific gravity of the solid phase, so that it is retained and carried within the two-phase laminar flow pattern, contamination between successive samples is avoided.

The reaction mixture stream, with the solid phase constantly circulating within the individual sample aliquots, is passed through an incubation coil 54 to enable the reaction to proceed. The output of incubation coil 54 is greatly diluted by buffer directed along conduit 53 and pump tube 57, to inhibit the reaction (i.e. quench the reaction) and facilitate washing of the solid phase by a dilution process. The output of incubation coil 54, is directed along conduit 56 to a wash station, identified as 58. Such wash station preferably includes a first magnetic trap 60 and a second magnetic trap 62, arranged with respect to conduit 56 in on-line fashion. Each of the magnetic traps 60 and 62 are electromagnetic and arranged to direct magnetic flux transversely to the path of the sample stream. The magnetic traps 60 and 62 are operated in particular timed sequence by programmer 64 controlled by a sample detector 65. Accordingly, sample detector 65 comprises light source 66 and a detector 68 and is located at the output of incubation coil 54. Light from source 66 is directed transversely through conduit 56. When a sample passing along conduit 56 intercepts such light, at time $t_1$ of FIG. 2, the reduced output level of a detector 68 instructs programmer 64 to energize the magnetic traps 60 and 62 concurrently.

When energized, first magnetic trap 60, in effect, sweeps the solid phase from each of the sample aliquots comprising, for example, sample $S_1$ as shown in FIG. 2. The intensity of the magnetic fields generated by the first magnetic trap 60 and, also, the second magnetic trap 62, as hereinafter described, are sufficient to ensure that passage of intra-sample air bubbles within sample S do not dislodge or carry away any of the solid phase retained within the wash station 58. Accordingly, the solid phase in each sample, albeit carried by individual aliquots, is accumulated along conduit 56 passing through the first magnetic trap 60. Energization of magnetic trap 62 at time $t_1$ ensures that any solid phase not swept by magnetic trap 60 is retained. Magnetic trap 60 is energized during passage of the entire volume of smaple S and, also, during passage of at least a portion of the following wash liquid segment, i.e. during time interval $t_1 - t_2$ shown in FIG. 2. Passage of such wash liquid segment through wash station 58, while the solid phase is packed, serves to remove any supernatant from the magnetic particles. Before the entire wash liquid segment has been passed, at time $t_2$, programmer 64 de-energizes magnetic trap 60. Accordingly, the solid phase is caused to be resuspended within the remaining wash liquid segment. Air bubbles in the wash liquid segment, as introduced along pump tubes 52, tend to break-up the solid phase packed by the magnetic trap 60 and accelerate resuspension of the same in the wash liquid to ensure complete removal of any liquid phase, i.e. unbound labelled or unlabelled antigens, from the surfaces thereof. As the second magnetic trap 62 is energized, the solid phase is again swept from the wash liquid segment.

In a particularly preferred embodiment of the invention, conduit 56 passing through the wash arrangement 58 is connected to the inlet of a three-port two-position valve 70, the outputs of such valve being connected to a solid-phase scintillation counter 72 (position I) and waste (position II), respectively. Also, an additional three-port, two position valve 76 is provided, having an inlet connected along conduit 78 to pump tube 80, whose inlet is connected to a source 82 of buffer, and having outlets connected to waste W (position I) and solid-phase counter 72 (position II). Valves 70 and 76 are controlled simultaneously by programmer 64. An additional air pump tube 84, having its inlet exposed to air, is connected to conduit 78, so as to periodically introduce air bubbles into the buffer stream flowed along conduit 78. The buffer liquid pumped along tube 78 is used for cleaning the solid-phase counter 72. As known, the presence of air bubbles along conduit 78 serves to accelerate the cleaning of any residues of a preceding sample withint the solid-phase counter. When the solid phase in magnetic trap arrangement 58 has been thoroughly washed and prior to the appearance of the next successive sample adjacent the light source 66, at time $t_3$ of FIG. 2, magnetic trap 62 is de-energized and valves 70 and 76 are operated momentarily to position I, to direct the solid phase, now suspended in wash liquid, to solid-phase counter 72 and the segmented buffer stream along conduit 78 to waste. At this time, the solid phase is passed through the storage coil 79 of solid-phase counter 72 and its radioactivity measured. Such measurements can be recorded, for example, by a print-out recorder 88. Subsequently, valves 70 and 76 are operated to position II, to direct the fluid stream along conduit 58 to waste and the segmented buffer stream along conduit 78 through the solid-phase counter, preparatory to the washing and measurement of the solid-phase in a next sample.

It will be evident that the liquid-phase can be measured, if desired, rather than the solid phase. To this end, a liquid-phase scintillation counter could be substituted for the solid-phase counter 72. In such event, the magnetic traps 60 and 62 are operated, as described, to sweep out the solid-phase from the aliquots of the same sample. Concurrently, valves 70 and 76 are controlled (to position I) to pass the separated liquid phae directly to the storage coil of the liquid-phase counter and while magnetic traps 60 and 62 are energized. Subsequently, valves 70 and 76 are operated to position II, prior to de-energization of magnetic traps 60 and 62, such that the solid-phase re-suspended in the wash liquid is passed to waste and the segmented buffer liquid is passed to wash the liquid-phase counter. In either event, it can be appreciated that the controlled specific gravity of the magnetic particles, on which the solid phase is immobilized, and the magnetic in-line trapping technique described, co-operate to achieve a positive separation of the solid and liquid phases, without deteriorating the wash characteristics of the system.

In accordance with another aspect of the invention (not illustrated), the individual samples passed along the conduit 28 may be reacted selectively. For example, we can provide a plurality of solid phase sources 20 and label sources 24, each having an associated pump tube 30 and return conduit 30′, each of which can be connected to a respctive three part, two-position changeover valve. The outputs of the changeover valves for each of the solid phase and label systems as well as the outputs of the buffer valves may be connected to corresponding inlets of a multi input/single output valve, whose output is connected to junctions A and B.

Each of the single output valves is controlled in response to information read from the individual receptacle 16, so as to introduce the appropriate solid phase and label phase, in phase with each other, at junctions B and A, so as to react selectively each sample. Also, the output on recoder 88 may be appropriately identified.

We claim:

1. Analysis apparatus, which comprises: means for flowing reaction mixtures, in turn, along a conduit and on a discrete basis, each of said reaction mixutures comprising a liquid phase including a fluid sample containing a constituent of interest and a solid phase comprising a first reagent bound to magnetically attractable particulate material, reaction taking place in the said mixture to form a reaction product, at least, on said particulate material; means along a portion of said conduit for magnetically trapping said particulate material in each of said reaction mixtures, so as to hold said solid phase against flow and separate said solid phase from the flowing liquid phase; and, downstream of said trapping means, means for determining said constituent of interest by selective analysis of said separated solid phase and/or said separated liquid phase.

2. Apparatus according to claim 1, which further includes: means for introducing said particulate material into admixture with each fluid sample flowing along said conduit.

3. Apparatus according to claim 1, wherein said trapping means comprises first magnetic means to provide a magnetic field in said portion of said conduit and substantially transverse of the direction of reaction mixture flow.

4. Apparatus according to claim 1, wherein said trapping means comprises first and second magnetic means to provide spaced magnetic fields in said portion of said conduit, said second magnetic means being downstream with respect to said first magnetic means.

5. Apparatus according to claim 4, which further includes: means for independently actuating said first and second magnetic means.

6. Apparatus according to claim 1, which further includes: means for passing wash liquid, at least, along said portion of said conduit intermediate said successive reaction mixtures.

7. Apparatus according to claim 3, which further includes: means for passing wash liquid, at least, along said portion of said conduit intermediate said successive reaction mixtures, and means for actuating said first magnetic means to hold said particulate material for washing by said wash liquid and, subsequently, de-actuating said first magnetic means to release said particulate material into suspension in said wash liquid.

8. Apparatus according to claim 5, which further includes: means for passing wash liquid, at least, along said portion of said conduit and intermediate said successive reaction mixtures, and wherein said actuating means includes means for actuating said first and second magnetic means concurrently to hold said particulate material for washing by said wash liquid and, subsequently, for selectively de-actuating said first magnetic means to release said particulate material held thereby into suspension in said wash liquid and be carried to said second magnetic means.

9. Apparatus according to claim 4, wherein each of said first and second magnetic means, when actuated, provide magnetic fields substantially transverse of the direction of reaction mixture flow in said conduit.

10. Apparatus according to claim 4, wherein each said first and second magnetic means is electromagnetic.

11. Apparatus according to claim 10, which further includes: means for degaussing each of said first and second magnetic means.

12. Apparatus according to claim 1, which further includes: means for successively flowing said reaction mixtures along said conduit, and means for introducing an occluding inert fluid segment intermediate successive reaction mixtures to maintain said successive reaction mixtures discrete.

13. Apparatus according to claim 12, which further includes: means for introducing additional occluding inert fluid segments into said conduit to sub-divide each of said reaction mixtures.

14. Apparatus according to claim 12, which further includes: means for providing a wash liquid segment between successive reaction mixtures flowing in said conduit, each of said reaction mixtures being separated from adjacent wash liquid segments by at least an occluding inert fluid segment.

15. Apparatus according to claim 1, which further includes: means for passing successive fluid samples along said conduit, and means for introducing said particulate material into said conduit on an intermittent basis.

16. Apparatus according to claim 15, which further includes: a source of said particulate material, and wherein said intermittent introducing means includes means for continuously pumping said particulate material from said source and for returning to said source said particulate material not admitted to said conduit.

17. Apparatus according to claim 15, which further includes: means for introducing buffer solution into said conduit alternately with said particulate material, so as to maintain the flow along said conduit substantially constant.

18. Apparatus according to claim 3, which further includes: means upstream of said portion of said conduit for detecting the passage of each of said reaction mixtures along said conduit, and means responsive to said detecting means for actuating said magnetic means to trap said particulate material in each said reaction mixture.

19. Apparatus according to claim 1, which further includes: means for providing a second reagent in each of said reaction mixtures.

20. Apparatus according to claim 1, which further includes: means for introducing a second reagent into admixture with each said reaction mixture flowing along said conduit.

21. Apparatus according to claim 1, further including, downstream of said trapping means, valving means in said conduit for selectively directing said separated solid phase or said separated liquid phase to said determining means.

22. Apparatus according to claim 1, wherein said determining means includes means for measuring radioactively, color, fluorescence or luminescence.

23. A method of analyzing a plurality of fluid samples for particulate constituents of interest, which comprises the steps of:
(a) forming a reaction mixture of each of said fluid samples, each reaction mixture comprising a liquid phase and a solid phase, said solid phase comprising a first reagent bound to magnetically attractable particulate material and reactive with the particular constituent to be analyzed in each said fluid sample to form a reaction product, at least on said particulate material;

(b) flowing each said reaction mixture in turn and on a discrete basis along a conduit;

(c) magnetically trapping said particulate material in each said reaction mixture during flow along a first portion of said conduit, so as to hold said particulate material and thereby separate said solid phase from said liquid phase; and (d) determining the constituent of interest in each said sample by selective analysis of said separated solid phase and/or said separated liquid phase.

24. A method according to claim 23, further comprising the step of: introducing said solid phase along said conduit into admixture with each said fluid sample.

25. A method according to claim 23, further comprising the step of passing wash liquid along, at least, said first portion of said conduit while trapping said particulate material.

26. A method according to claim 25, further comprising the step of: re-suspending said trapped particulate material into said wash liquid.

27. A method according to claim 26 wherein, said re-suspended particulate material is carried to a second portion of said conduit downstream of said first portion, and further comprising the steps of: magnetically trapping said particulate material at said second portion of said conduit, passing wash liquid along said second portion of said conduit while trapping said particulate material, and re-suspending said trapped particulate matter into said wash liquid.

28. A method according to claim 23, further comprising the steps of: releasing said trapped particulate material, and separately collecting said released particulate matter.

29. A method according to claim 23, wherein said particulate material is trapped using at least one or more electromagnetic means, and comprising the further step of: degaussing said electromagnetic means upon release of said trapped particulate material.

30. A method according to claim 23, comprising the further step of: passing said reaction mixtures successively along said conduit, and introducing at least an occluding inert fluid segment intermediate successive reaction mixtures, so as to maintain said successive reaction mixtures discrete.

31. A method according to claim 30, comprising the further step of: introducing additional occluding inert fluid segments into said conduit to split each of said reaction mixtures into two or more segments.

32. A method according to claim 30, comprising the further step of: providing a wash liquid segment between successive reaction mixtures in said conduit, each said reaction mixture being separated from adjacent was liquid segments by at least an inert fluid segment.

33. A method according to claim 30, comprising the further step of: introducing said particulate material into said conduit on an intermittent basis to merge with said successive fluid samples.

34. A method according to claim 33, comprising the further step of: introducing buffer solution into said conduit alternately with said particulate material to maintain flow along said conduit substantially constant.

35. A method according to claim 30, comprising the further step of: providing a second reagent into each said reaction mixture.

36. A method according to claim 35, further including the step of: introducing said second reagent into admixture with each of said fluid samples flowing along the conduit.

37. Apparatus according to claim 1, wherein the fluid samples are human or animal samples.

38. Apparatus according to claim 37, wherein the constituent of interest is an antigen, antibody, or antigen:antibody complex.

39. Apparatus according to claim 19, wherein said constituent of interest is an antigen, said first reagent is an antibody to said antigen, and said second reagent is an antigen which can bind with the antibody and which carries an indentifying label.

40. Apparatus according to claim 19, wherein said constituent of interest is an antibody, said first reagent is an antigen capable of binding with said antibody, and said second reagent is an antibody which is capable of binding with said antigen and which carries an identifying label.

41. Apparatus according to claim 39, wherein the said label is a radioactive atom, a fluorescent group, an enzyme or co-enzyme, or a chemiluminescent material.

42. Apparatus according to claim 19, wherein said second reagent comprises a predetermined amount of substance which reacts with said constituent of interest to form therewith a complex, and wherein said first reagent binds with the said complex or with excess unreacted second reagent.

43. Apparatus according to claim 19, wherein said second reagent carries a radioactive label.

44. Apparatus according to claim 1, wherein said first reagent bound to said particulate material is a virus or an immunoglobulin.

45. Apparatus according to claim 1, wherein said particulate material is of a composite structure.

46. Apparatus according to claim 45, wherein said particulate material comprises a matrix containing magnetically attractable material.

47. Apparatus according to claim 46, wherein said matrix comprises an organic material capable of binding to said first reagent.

48. Apparatus according to claim 1, wherein said particulate material has a specific gravity close to that of said reaction mixture.

49. Apparatus according to claim 48, wherein the specific gravity of said particulate material is substantially in the range of 1.4 to 3.2.

50. Apparatus according to claim 40, wherein the said label is a radioactive atom, a fluorescent group, an enzyme or co-enzyme, or a chemiluminescent material.

51. A method of analyzing a plurality of fluid samples for particular constituents of interest, which comprises the steps of:

(a) forming a reaction mixture of each of said fluid samples, said reaction mixture comprising magnetically attractable particulate material and a reagent reactive with a particular constituent to be analyzed to form a reaction product, at least a portion of said reaction product being bound to said particulate material;

(b) flowing each said reaction mixture in turn and on a discrete basis along a conduit;

(c) magnetically trapping said particulate material in each said reaction mixture along a portion of said conduit, so as to separate said particulate material from said reaction mixture; and (d) determining said constituent of interest by selective analysis of said separated particulate material and/or said separated reaction mixture.

52. A method as defined in claim 51, including the further steps of: passing said fluid samples along said conduit on a successive basis, separating successive fluid samples by at least an inert fluid segment, so as to maintain said fluid samples discrete, and introducing said reagent and said particulate material on an intermittent basis to merge with said fluid samples to form said reaction mixtures.

53. A method as defined in claim 51, comprising the further step of: forming said particulate material to have a specific gravity substantially equal to that of said reaction mixture.

54. A method according to claim 51, comprising the further steps of: passing said reaction mixtures successively along said conduit, and introducing, at least, an occluding inert fluid segment intermediate successive reaction mixtures, so as to maintain said successive reaction mixtures discrete.

55. A method according to claim 51, comprising the further step of: providing a wash liquid segment between said successive reaction mixtures, each of said reaction mixtures being separated from adjacent wash liquid segments by at least an inert fluid segment.

56. A method according to claim 51, comprising the further step of: maintaining said particulate material magnetically trapped during passages of at least a portion of said wash liquid segment along said conduit portion.

57. A particulate material for use in the analysis of a liquid sample of known specific gravity, said particulate material comprising a reagent and one or more magnetic particles in a matrix of binding material, said particulate material having a controlled specific gravity approaching that of said liquid sample so as to retard separation of said particulate material when mixed with said liquid sample, said binding material being selected from a group consisting of: cellulose or a cellulose derivative, a polymer or synthetic polymeric material, and agarose.

58. The particulate material of claim 57, wherein said specific gravity of said particulate material is approximately equal to 1.4.

59. The particulate material of claim 57, wherein the magnetic particles are selected from a group consisting of iron, magnetic iron oxides, nickel, cobalt or chromium oxide.

60. The particulate material of claim 57, wherein said reagent is selected from a group consisting of an antigen, an antibody or biological substance.

61. The particulate material of claim 57, wherein said reagent is an antigen and said liquid sample comprises an antibody for reaction with said antigen.

62. The particulate material of claim 57, wherein said reagent is an antibody and said liquid sample comprises an antigen for reaction with said antibody.

63. A method of immunoassaying a sample, comprising the steps of:
mixing:
（a) a sample defining a liquid phase, and
(b) a reagent combined with a magnetically attractable particulate defining a solid phase,
forming said solid phase to have a specific gravity so as to tend to be suspended within said liquid phase upon mixing of said phases, such that separation of the two phases is retarded and reactivity of the sample with said reagent is enhanced,
magnetically separating said liquid and said solid phases following reaction of said sample with said reagent, and
measuring a reaction product of said sample and said reagent in said separated solid and/or said liquid phase.

64. The method of claim 63, comprising the further step of forming said solid phase to have a specific gravity approximately equal to the specific gravity of said liquid phase.

65. The method of claim 63, comprising the further step of forming said solid phase to have a specific gravity approximately equal to 1.4.

66. The method of claim 63, wherein said reagent is an antigen, and comprising the step of combining an antibody with said particulate to define said solid phase.

67. The method of claim 63, wherein said reagent is an antibody, and comprising the further step of combining an antigen with said particulate to define said solid phase.

* * * * *